US00PP18134P2

(12) United States Plant Patent
Goffreda et al.

(10) Patent No.: US PP18,134 P2
(45) Date of Patent: Oct. 23, 2007

(54) PEACH TREE NAMED 'NJ353'

(50) Latin Name: ***Prunus persica* L.**
Varietal Denomination: NJ353

(75) Inventors: Joseph C. Goffreda, Manapalan, NJ (US); Anna M. Voordeckers, East Windsor, NJ (US)

(73) Assignee: Rutgers, The State University, New Brunswick, NJ (US)

( * ) Notice: Subject to any disclaimer, the term of this patent is extended or adjusted under 35 U.S.C. 154(b) by 0 days.

(21) Appl. No.: 11/392,122

(22) Filed: Mar. 29, 2006

(51) Int. Cl.
*A01H 5/00* (2006.01)

(52) U.S. Cl. ..... Plt./198

(58) Field of Classification Search ..... Plt./198
See application file for complete search history.

*Primary Examiner*—Anne Marie Grunberg
*Assistant Examiner*—S. B. McCormick-Ewoldt
(74) *Attorney, Agent, or Firm*—Michael J. Medley; Driggs, Hogg & Fry Co., L.P.A.

(57) ABSTRACT

A new and distinct peach variety of *Prunus persica* named 'NJ353' is provided. This variety is distinguished from other peach varieties by its unique combination of showy flowers, fruit that ripen in late-season, attractive fruit with a yellow-orange ground color, freestone fruit with a juicy, melting texture and moderately acidic flavor, and good production of firm fruit that maintain their eating quality following cold storage.

6 Drawing Sheets

Latin name of genus and species of the plant claimed: *Prunus persica* L.
Variety denomination: 'NJ353'.

BACKGROUND OF THE INVENTION

The present invention relates to a new and distinct variety of peach tree named 'NJ353'. Our new tree resulted from crossing 'Biscoe' as the seed parent with 'Fairtime' peach tree, as the pollen parent. The new variety differs from seed parent 'Biscoe' (unpatented) in that the new variety has large, showy flowers and firm fruit that ripen in late-season, while the seed parent has small, nonshowy flowers and comparatively soft fruit that ripen in the latter part of mid-season. The new variety differs from pollen parent 'Fairtime' (unpatented) in that the new variety has more cold tolerance and has consistently developed a greater percentage of red over color than the pollen parent. The resulting tree was selected when growing in a cultivated area as the $122^{nd}$ tree in the $47^{th}$ row of Block G in Cream Ridge, N.J.

BRIEF SUMMARY OF THE INVENTION

The 'NJ353' variety is distinguished from other peach varieties due to the following unique combination of characteristics:

- Attractive round fruit with a slightly depressed apex point.
- Fruit with an attractive yellow-orange ground color.
- Good production of firm fruit that ripen in late-season.
- Fruit have above average eating quality following cold storage.

The variety was asexually reproduced at the Rutgers Fruit Research and Extension Center in Cream Ridge, N.J. Asexual reproduction of this new variety by budding onto 'Lovell' rootstock (unpatented) shows that the foregoing characteristics are so reproduced.

The following detailed description concerns the original tree, 'NJ353'. The original tree and asexual progeny have been observed growing in a cultivated area in Cream Ridge, N.J. Certain characteristics of this variety, such as growth and color, may change with changing environmental conditions (such as, light, temperature, moisture, nutrient availability) or other factors. Color descriptions and other terminology are used in accordance with their ordinary dictionary descriptions, unless the context clearly indicates otherwise. Color designations are made with reference to The Royal Horticultural Society (R.H.S.) Colour Chart.

BRIEF DESCRIPTION OF THE DRAWINGS

This new variety is illustrated by the accompanying photographic drawings, depicting the peach tree by the best possible color representation using color photography. Colors are approximate as color depends on horticultural practices, such as light level, fertilization rate, and other conditions and, therefore, the color characteristics of this new variety should be determined with reference to the observations described herein, rather than from these illustrations alone.

DETAILED BOTANICAL DESCRIPTION

Figure 1:
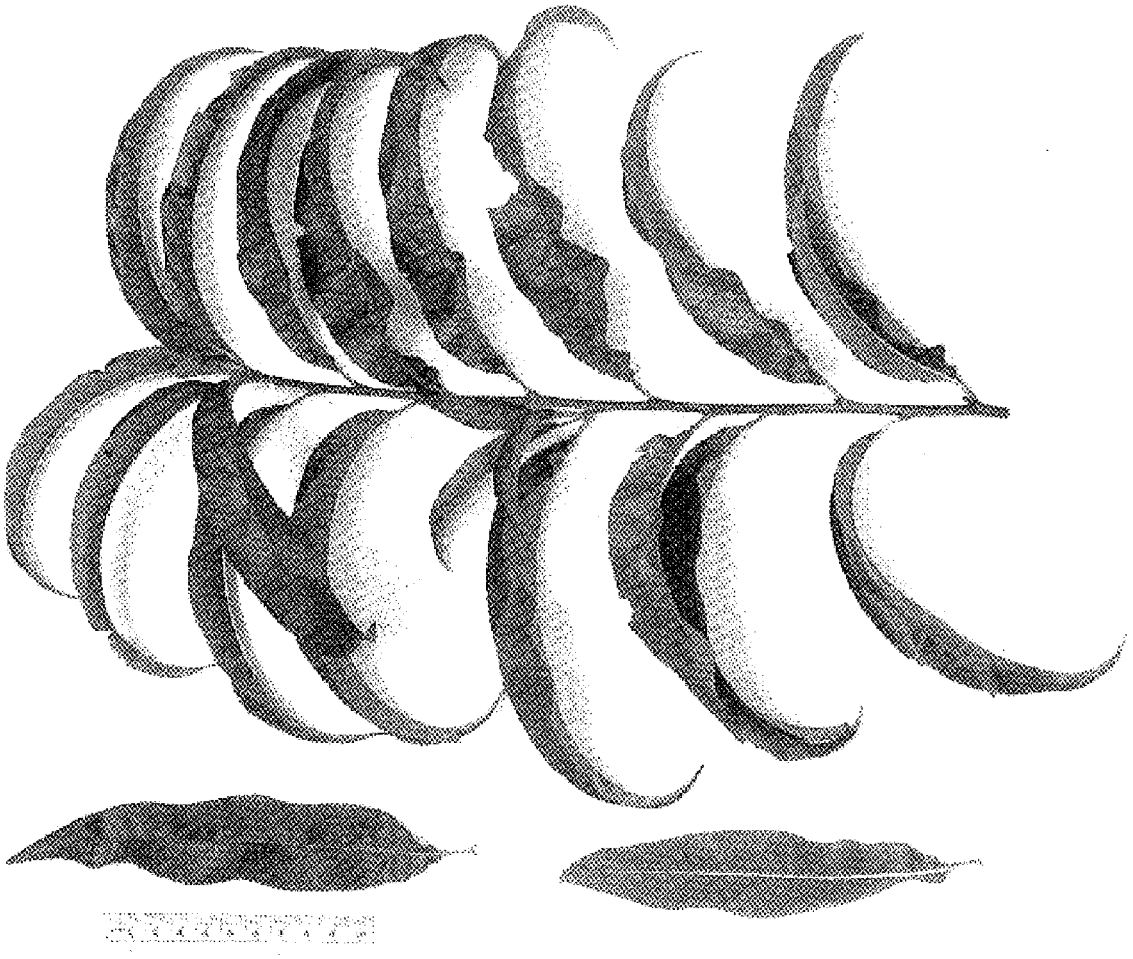
FIG. 1 is a color photograph taken on Aug. 29, 2005 of a characteristic twig of 'NJ353' in late summer bearing typical leaves of the mature foliage.
Figure 2:
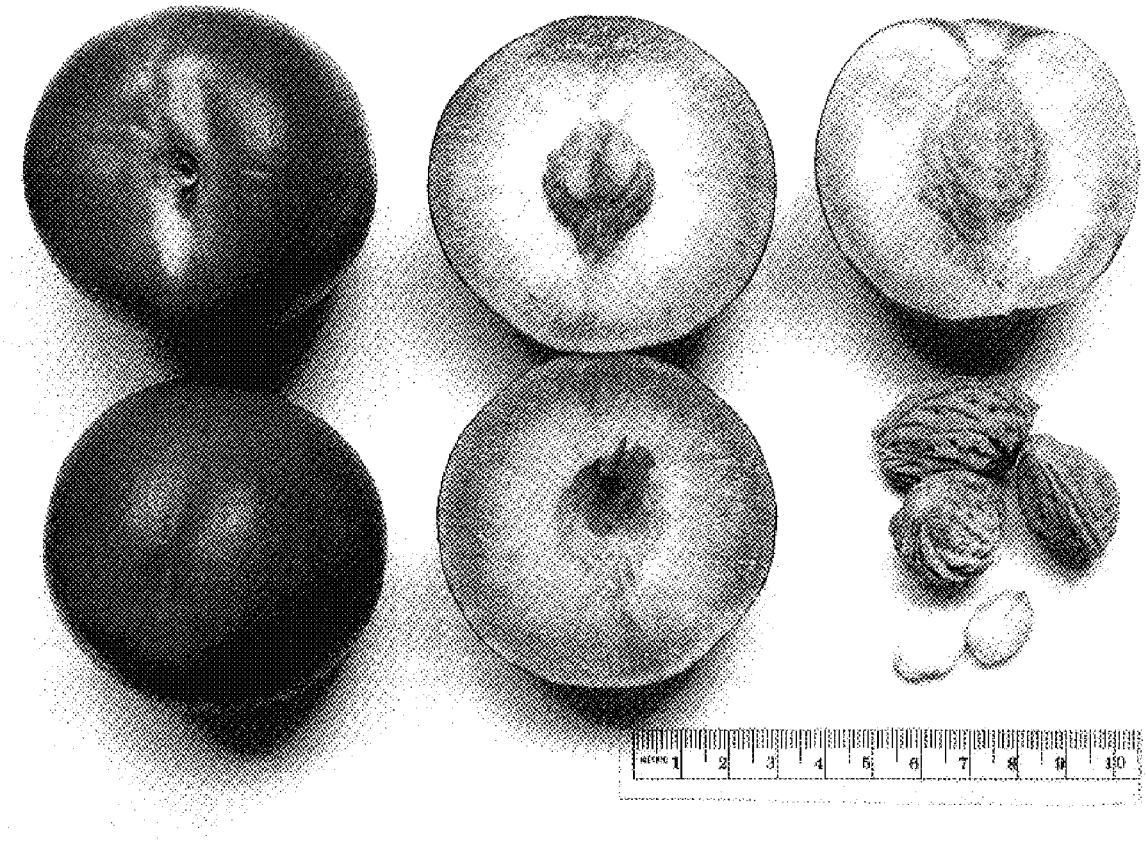
FIG. 2 is a color photograph taken on Sep. 10, 2004 of characteristic mature fruit and stones of 'NJ353'. Whole fruit are presented in three positions and a transverse cross section to show that the pericarp does not adhere to the pit when the fruit is mature. The stones illustrate the obovoid shape and the pit grooves on the surface of the stone.
Figure 3:
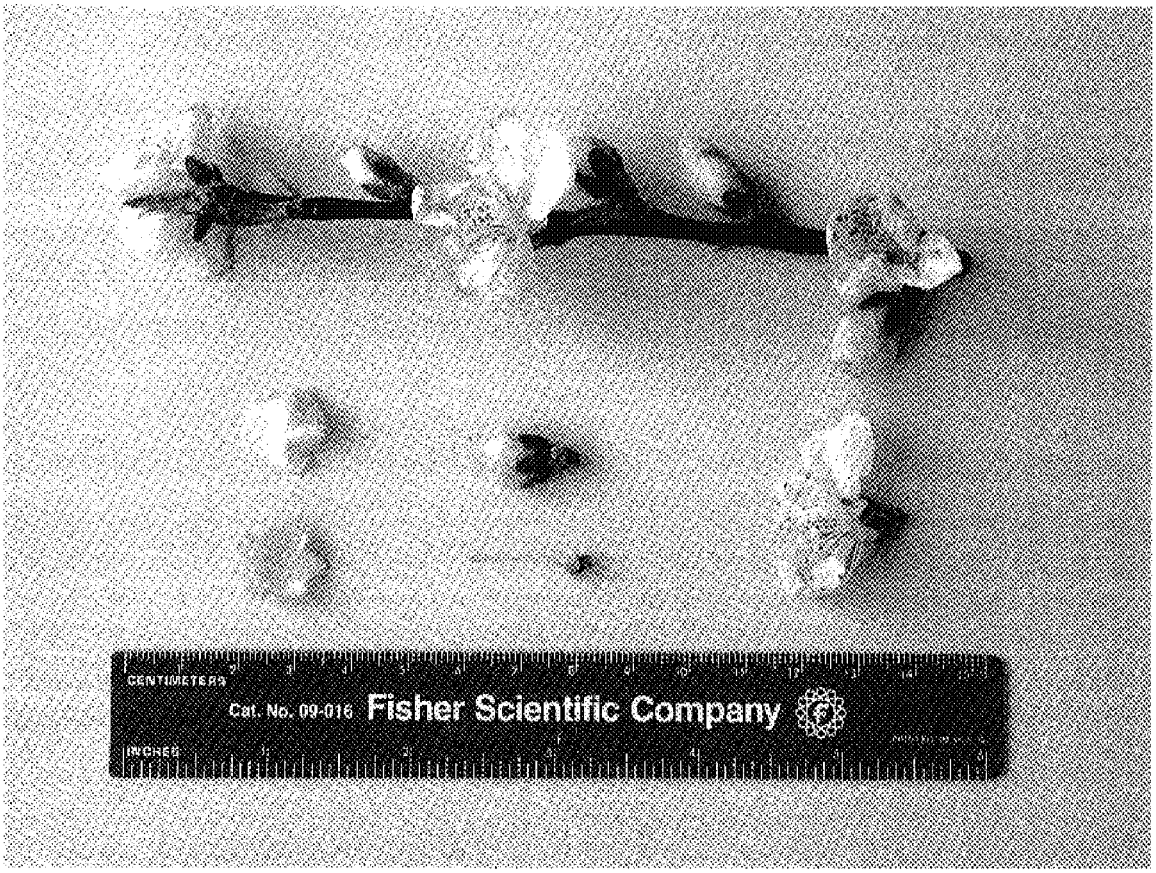
FIG. 3 is a color photograph of a characteristic twig that illustrates the typical flower buds and large, showy flowers of 'NJ353' observed on a tree in Cream Ridge, N.J. on Apr. 21, 2004.
Figure 4:
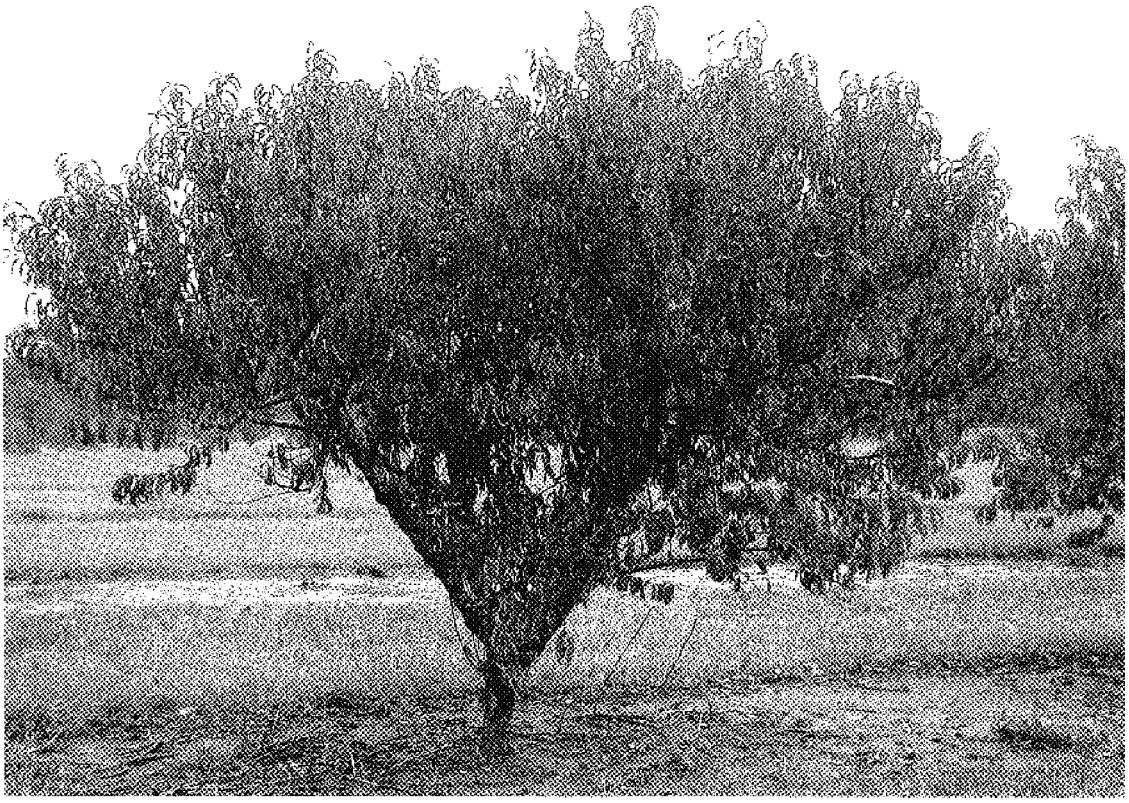
FIG. 4 is a color photograph of a tree of 'NJ353' in early fall that illustrates the spreading growth habit of a tree in Cream Ridge, N.J. on Oct. 27, 2005.
Figure 5:
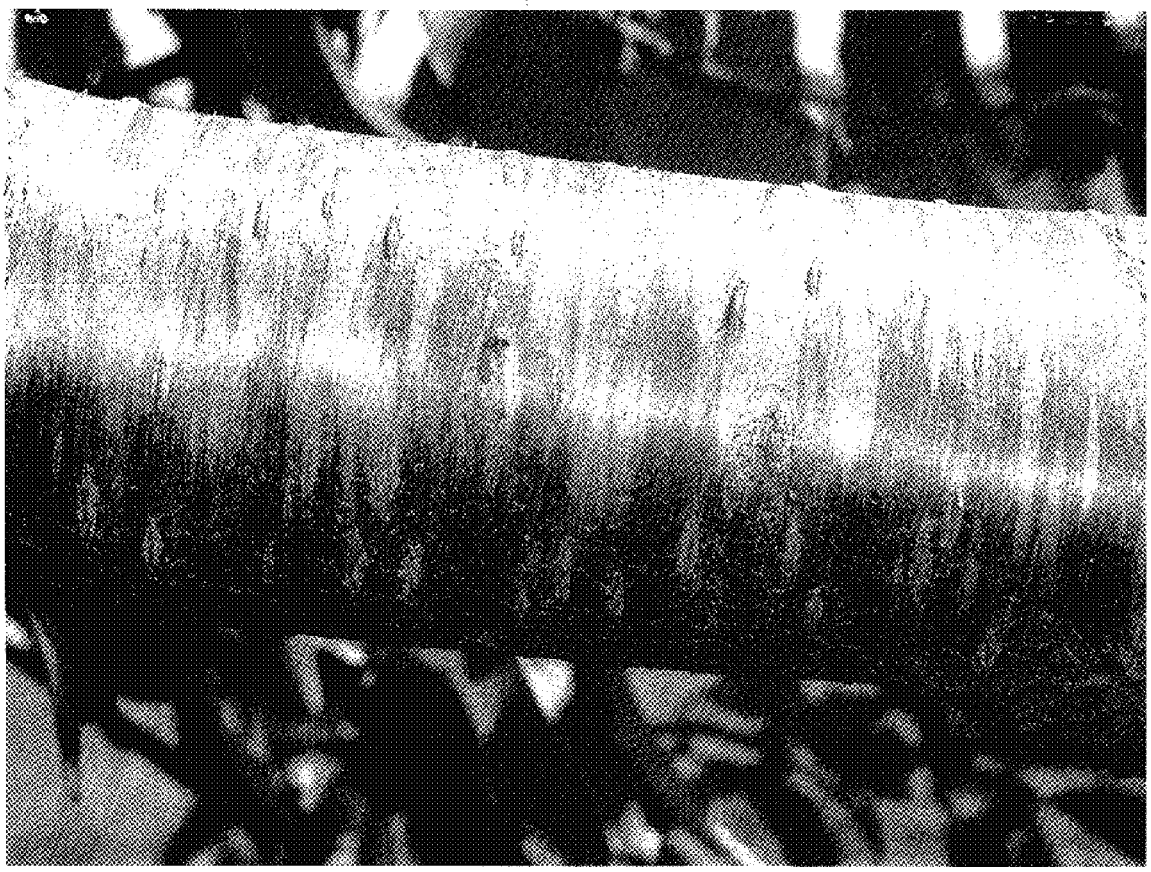
FIG. 5 is a color photograph taken on Oct. 27, 2005 of immature bark of 'NJ353' that illustrates color and the comparatively low density of elliptical lenticels with a greyed-white border on the immature bark.
Figure 6:
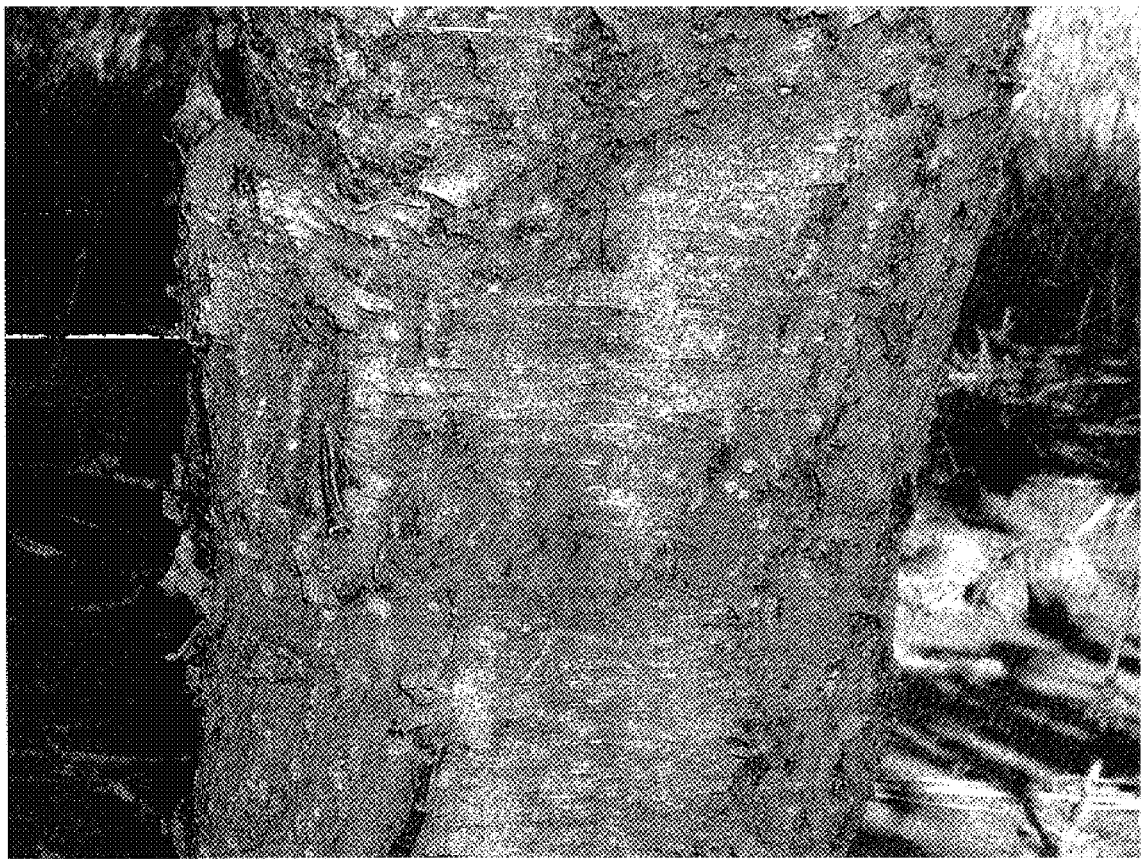
FIG. 6 is a color photograph taken on Oct. 27, 2005 of mature bark of 'NJ353' that illustrates the moderately rough texture of the mature bark.

The following detailed description of the 'NJ353' variety is based on observations of an asexually reproduced tree. The observed tree was nine years of age and growing on 'Lovell' seedling rootstock (unpatented) in Research Block C in Cream Ridge, N.J.

Scientific name: *Prunus persica* L.
Parentage:

| | |
|---|---|
| Seed parent: | Biscoe. |
| Pollen parent: | Fairtime. |

Tree:

| | |
|---|---|
| Vigor: | Moderately vigorous. |
| Plant hardiness zone: | Growth of plants has only been observed in zone 6b. |
| Dormant flower bud cold tolerance: | At least to −15° C. |
| Overall shape: | Spreading. |
| Height: | Slightly below average as compared to other peach cultivars. For example, measurement of a typical grafted tree on 'Lovell' seedling rootstock (unpatented) at nine years after planting shows an average height of 3.4 meters when grown in Cream Ridge, New Jersey. |
| Width: | Average as compared to other peach cultivars. For example, measurement of a typical grafted tree on 'Lovell' seedling rootstock (unpatented) at nine years after planting shows an average width of 5.2 meters when grown in Cream Ridge, New Jersey. |
| Caliper: | Nine year old tree is 51 cm in circumference measured at 20 cm from the ground. |
| Pollination requirements: | Self-pollinating |

Trunk and branches:

| | |
|---|---|
| Trunk bark texture: | Moderately rough. |
| Trunk bark color: | Greyed-white (RHS 156c). |
| Primary branches: | Branches that are approximately 15 cm in circumference are greyed-orange (RHS 176a) in color, overlaid with grey (RHS 201d). |
| Lenticels: | Low density, approximately 1 per square cm; elliptical shape; typical examples of which measured 5.5 mm in length and 2.0 mm in width; greyed-orange (RHS 164a) in color and bordered with greyed-white (RHS 156b). |
| Branch pubescence: | None. |
| New growth bark: | Color varies between greyed-red (RHS 178a) and greyed-purple (RHS 183a) in sun; color yellow-green (RHS 152b) in shade. |
| Internodes: | Length averaging 21.2 mm on a one-year shoot. |

Leaves:

| | |
|---|---|
| Texture: | Glabrous. |
| Sheen: | Young leaves semi-glossy with a flat finish on the underside. |
| Length: | About 167 mm to 190 mm, averaging about 174 mm including the petiole. |
| Width: | About 34 mm to 46 mm, averaging about 39 mm. |
| Petiole: | Averaging 10.6 mm long and about 1.5 mm in diameter. |
| Margin: | Serrulate. |
| Margin undulation: | Slight. |
| Form: | Elliptic. |
| Apex: | Acuminate, curved downward. |
| Base: | Cuneate. |
| Venation: | Pinnate. |
| Glands: | |
| Number: | About 3 to 6, averaging about 4. |
| Position: | Located on the leaf margin and petiole. |
| Size: | Length averaging 1.4 mm and width averaging 1.1 mm. |
| Form: | Reniform. |
| Stipules: | None observed on mature leaves. |
| Leaf Color: | |
| Upper leaf surface: | Between green (RHS 137a) and yellow-green (RHS 147a). |
| Lower leaf surface: | Yellow-green (RHS 147b). |
| Vein: | Greyed-yellow (RHS 160c). |
| Pubescence: | None. |

Flowers:

| | |
|---|---|
| Size: | Large size, typical flower measuring between 36 mm to 43 mm, averaging about 39 mm across. |
| Color: | |
| Dormant bud: | Grey (between RHS 201a and RHS 201b). |
| Pink stage bud: | Red-purple (between RHS 62c and RHS 62d). |
| Open flower: | Young open flowers red (RHS 62d), with red venation (between RHS 56b and RHS 55c) at petal fall. |
| Petals: | Typically five petals per flower, cupped and round in shape; averaging about 18.0 mm long and 17.0 mm wide. Red (RHS 62d) in color. |
| Petal apex: | Obtuse. |
| Petal base: | Attenuate. |
| Stamens: | |
| Number: | Variable, typical range 36 to 41, averaging 38.8. |
| Length: | Variable, between 10.5 mm to 16.5 mm, averaging 13.9 mm. |
| Filament color: | White (RHS 155a). |
| Anther color: | Red (RHS 34b). |
| Pistil: | |
| Number: | One. |
| Size: | Length between 18.1 and 19.8 mm, averaging about 19.1 mm. |
| Pistil color: | Yellow-green (RHS 153a). |
| Ovary: | Moderate pubescence and ellipsoid in shape. |
| Sepals: | |
| Number: | Five. |
| Pubescence: | Short and moderate density. |
| Color: | Yellow-green (RHS 152c) with a greyed-red (RHS 178a) over color. |
| Shape: | Triangular, with a rounded apex. |
| Size: | Length averaging 5.4 mm, width averaging 4.8 mm. |
| Nectar cup color: | Greyed-orange (RHS 167b). |
| Pollen: | Abundant; yellow-orange (RHS 20a) in color. |
| Fragrance: | Very slight. |
| Bloom season: | Onset of bloom in 2005 on April 16; full bloom on April 19. |

Fruit:

| | |
|---|---|
| Size: | Large, averaging about 6.9 cm long, 7.2 cm wide parallel to the suture and 7.3 cm wide perpendicular to the suture. |
| Typical weight: | 201 g. |
| Form: | |
| Longitudinal section: | Nearly round. |
| Traverse section: | Round. |
| Suture: | Very shallow, extending from the base to apex. |
| Ventral surface: | Typically smooth. |
| Base: | Round. |
| Apex: | Flat, apex point slightly depressed. |
| Stem: | Average length of 6.1 mm and an average diameter of 5.6 mm. |
| Skin: | |
| Thickness: | Average. |
| Surface: | Regular with short pubescence. |
| Tenacity: | Average. |
| Astringency: | None. |
| Tendency to crack: | Low. |
| Color: | Mottled greyed-purple (RHS 183a) over a red (RHS 46a) blush; ground color yellow-orange (RHS 16b). |
| Fruit Properties: | |
| Flesh color: | Yellow-orange (between RHS 16a and RHS 16b). |
| Flesh adhesion: | Freestone. |
| Juice: | Moderate. |
| Texture: | Firm, but melting. |
| Fibers: | Not noticeable. |
| Ripens: | Between September 4 and September 17 at Cream Ridge, New Jersey. |
| Flavor: | Average to above average, moderately acidic. |
| Soluble solids: | 12.8%. |
| Aroma: | Very slight. |
| Eating quality: | Good. |
| Keeping quality: | Above average. Has held its flavor and firmness for at least 21 days in cold storage at 1° C. to 4° C. |
| Shipping quality: | Very good. Fruit are generally very firm at harvest. No bruising or scaring disorders have been observed. |
| Usage: | Dessert. |
| Market: | Local and long distance. |
| Productivity: | Good. Trees have produced a crop in 9 out of 11 years and a full crop in 4 out of 11 years at Cream |

-continued

| | |
|---|---|
| | Ridge, New Jersey. |

Stone:

| | |
|---|---|
| Type: | Freestone. |
| Form: | Obovoid. |
| Base: | Narrow. |
| Apex: | Medium. |
| Surface: | Pit grooves. |
| Ventral suture: | Medium, truncated at the apex. |
| Dorsal ridge: | Medium height, narrow width, with lines of medium depth. |
| External color: | Greyed-orange (between RHS 166b and RHS 166c) overlaid with greyed-purple (RHS 183d). |
| Internal color when cracked: | Greyed-orange (between RHS 165c and RHS 165d). |
| Cavity surface color: | Greyed-orange (RHS 165c). |
| Average stone dry weight: | 6.8 g. |
| Average stone wall thickness: | Varies between 7.1 and 9.4 mm. |
| Size: | Averages about 37 mm long, 26.6 mm wide parallel to the dorsal ridge, and 18.6 mm wide perpendicular to the dorsal ridge. |
| Tendency to split: | Low. |
| Kernel: | |
| Form: | Ovate. |
| Skin color: | Greyed-orange (between RHS 165a and RHS 165b). |
| Vein color: | Greyed-orange (between RHS 164a). |
| Viability: | Yes. |
| Size: | Averages about 18.3 mm long, 11.8 mm wide, and 4.5 mm in breadth. |

Plant/fruit disease and pest resistance/susceptibility: No atypical resistances/susceptibilities have been noted under normal cultural practices.

We claim:

1. A new and distinct variety of peach tree, substantially as herein shown and described.

* * * * *